(12) United States Patent
Shiraki

(10) Patent No.: US 7,757,568 B2
(45) Date of Patent: Jul. 20, 2010

(54) FLOWMETER FOR FINE CHANNEL, ANALYZER USING THE SAME, AND CARTRIDGE FOR ANALYZER

(75) Inventor: Yasunori Shiraki, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 11/991,580

(22) PCT Filed: Sep. 6, 2006

(86) PCT No.: PCT/JP2006/317608

§ 371 (c)(1),
(2), (4) Date: Mar. 6, 2008

(87) PCT Pub. No.: WO2007/029720

PCT Pub. Date: Mar. 15, 2007

(65) Prior Publication Data

US 2009/0126505 A1 May 21, 2009

(30) Foreign Application Priority Data

Sep. 6, 2005 (JP) .............................. 2005-258174

(51) Int. Cl.
*G01F 1/58* (2006.01)
(52) U.S. Cl. ................................... 73/861.15
(58) Field of Classification Search ............. 73/861.15, 73/61.71; 324/439, 449; 204/403.02
See application file for complete search history.

(56) References Cited

U.S. PATENT DOCUMENTS

| 3,820,392 | A | 6/1974 | Beck et al. |
| 4,559,831 | A | 12/1985 | Prestele |
| 5,220,920 | A | 6/1993 | Gharib |
| 6,122,956 | A * | 9/2000 | Klausner et al. ............ 73/61.71 |
| 7,144,485 | B2 * | 12/2006 | Hsu et al. ............... 204/403.02 |
| 2002/0092363 | A1 | 7/2002 | Jorgenson et al. |

FOREIGN PATENT DOCUMENTS

| JP | 57-94625 | 6/1982 |
| JP | 60-33055 | 2/1985 |
| JP | 2005-140756 | 6/2005 |

* cited by examiner

*Primary Examiner*—Jewel Thompson
(74) *Attorney, Agent, or Firm*—Hamre, Schumann, Mueller & Larson, P.C.

(57) ABSTRACT

A fine channel flowmeter A1 is provided for measuring the amount of a blood sample DS through a channel 10. The flowmeter includes at least two electrode groups 62Aa, 62Ab each including a pair of electrodes 62*a*, 62*b*, and a conduction detector 7 for detecting electrical conduction between the paired electrodes 62*a*, 62*b* included in each of the electrode groups 62Aa, 62Ab. Each of the electrodes 62*a*, 62*b* is exposed in the channel 10 at least partially, and the electrode groups 62Aa, 62Ab are spaced from each other in the flow direction of the channel 10.

12 Claims, 12 Drawing Sheets

FLOWMETER FOR FINE CHANNEL, ANALYZER USING THE SAME, AND CARTRIDGE FOR ANALYZER

TECHNICAL FIELD

The present invention relates to a flowmeter for measuring the amount of e.g. a blood sample flowing through a very narrow channel in analyzing a particular component contained in the blood sample. The invention also relates to an analyzer using such a flowmeter, and an analyzer cartridge, in particular, a disposable analyzer cartridge.

BACKGROUND ART

Analyzing a particular component in blood is an effective way to check the condition of a human body or cure a particular disease. For such analysis, use may be made of an analyzer to which a cartridge formed with a fine channel is mounted. To count blood cells such as red blood cells or white blood cells in the blood sample flowing through the fine channel, it is necessary to accurately measure the flow of the blood sample in the cartridge. To grasp the flow accurately, it may be considered to provide the analyzer with e.g. a constant-flow pump as a means to move the blood sample. However, since the cartridge is formed with a fine channel, variation in pressure drop resistance in the flow direction is large. Thus, it is difficult to achieve the constant flow only by a pump. Thus, it is preferable to provide a means for measuring the flow of the blood sample through the fine channel of the cartridge.

FIG. 15 shows a conventional fine channel flowmeter. The flowmeter X shown in the figure measures the flow of the fluid 93 through a channel 92 formed in a substrate 91. Specifically, the flowmeter X measures the flow of the fluid 93 by using an excitation laser beam 94a irradiated through a lens 94 and a detection laser beam 95a irradiated through a lens 95. The excitation laser beam 94a may be infrared to heat the fluid 93 flowing through the channel 92. The detection laser beam 95a may be visible light having a wavelength of e.g. 532 nm. The detection laser beam 95a passed through the fluid 93 is received by a light-receiving apparatus 98 via an infrared filter 96 and a pinhole plate 97. Signals from the light-receiving apparatus 98 are processed by a controller 99. By this process, the index of refraction of the fluid 93 at the portion irradiated with the detection laser beam 95a is computed immediately. The index of refraction of the fluid 93 changes when the fluid is irradiated with the excitation laser beam 94a. The period of time from when the irradiation of the excitation laser beam 94a is started till when a change in index of refraction of the fluid 93 is detected is measured. Based on the period of time and the distance between the irradiation position of the excitation laser beam 94a and that of the detection laser beam 95a, the flow velocity of the fluid 93 through the channel 92 is obtained. By multiplying the flow velocity by the cross sectional area of the channel 92, the flow of the fluid 93 is obtained.

However, to meet the strong demand for size reduction of the cartridge to which the flowmeter X is to be mounted, the cross section of the channel 92 is made small. The smaller the cross section of the channel 92 is, the more necessary it is to converge the excitation laser beam 94a and the detection laser beam 95a into a small spot light and to enhance the accuracy of the irradiation position. That is, the light sources (not shown) of the excitation laser beam 94a and the detection laser beam 95a need to be reduced in size, which makes the manufacture of the analyzer cartridge difficult. In this way, the size reduction of the analyzer cartridge is hindered.

Patent Document 1: JP-A-2005-140756

DISCLOSURE OF THE INVENTION

Problems to be Solved by the Invention

An object of the present invention, which is proposed under the above-described circumstances, is to provide a flowmeter capable of properly measuring the amount of a fluid through a fine channel and suitable for size reduction, while also providing an analyzer utilizing such a flowmeter, and an analyzer cartridge.

Means for Solving the Problems

According to a first aspect of the present invention, there is provided a fine channel flowmeter for measuring the amount of fluid through a fine channel. The flowmeter comprises at least two electrode groups each including a pair of electrodes, and a conduction detector for detecting electrical conduction between the paired electrodes included in each of the electrode groups. Each of the electrodes is exposed in the fine channel at least partially, and the electrode groups are spaced from each other in the flow direction of the fine channel.

In a preferred embodiment of the present invention, the paired electrodes are spaced from each other in the width direction of the fine channel.

According to a second aspect of the present invention, there is provided a fine channel flowmeter for measuring the amount of fluid through a fine channel. The flowmeter comprises at least two electrodes and a conduction detector for detecting electrical conduction between the at least two electrodes. The at least two electrodes are exposed in the fine channel at least partially and spaced from each other in the flow direction of the fine channel.

In a preferred embodiment of the present invention, the fine channel flowmeter further comprises a common electrode arranged upstream from the at least two electrodes in the flow direction of the fine channel and is configured to come into contact with the fluid at least partially. The conduction detector is further capable of detecting electrical conduction between the common electrode and each of the electrodes.

According to a third aspect of the present invention, there is provided an analyzer for analyzing a particular component contained in a sample liquid. The analyzer comprises an analysis portion for analyzing the particular component, a fine channel connected to the analysis portion, and a fine channel flowmeter provided by the first or the second aspect of the present invention for measuring the amount of the sample liquid through the fine channel.

According to a fourth aspect of the present invention, there is provided an analyzer cartridge to be mounted to an analyzer for analyzing a particular component contained in a sample liquid. The cartridge comprises an analysis portion for analyzing the particular component, a fine channel connected to the analysis portion, and electrode groups used for a fine channel flowmeter provided by the first or the second aspect of the present invention for measuring the amount of the sample liquid through the fine channel.

In a preferred embodiment, the cartridge includes a main body in the form of a flat plate in which the fine channel is formed to penetrate. The electrode penetrates from a surface of the main body to the fine channel.

In a preferred embodiment of the present invention, the cartridge includes a main body in the form of a flat plate formed with a groove for defining the fine channel, and a printed wiring board bonded to a surface of the main body on the side formed with the groove. The electrode comprises a through-hole electrode formed in the printed wiring board.

Other features and advantages of the present invention will become more apparent from the detailed description given below with reference to the accompanying drawings.

BEST MODE FOR CARRYING OUT THE INVENTION

Preferred embodiments of the present invention will be described below with reference to the accompanying drawings.

Figure 1:
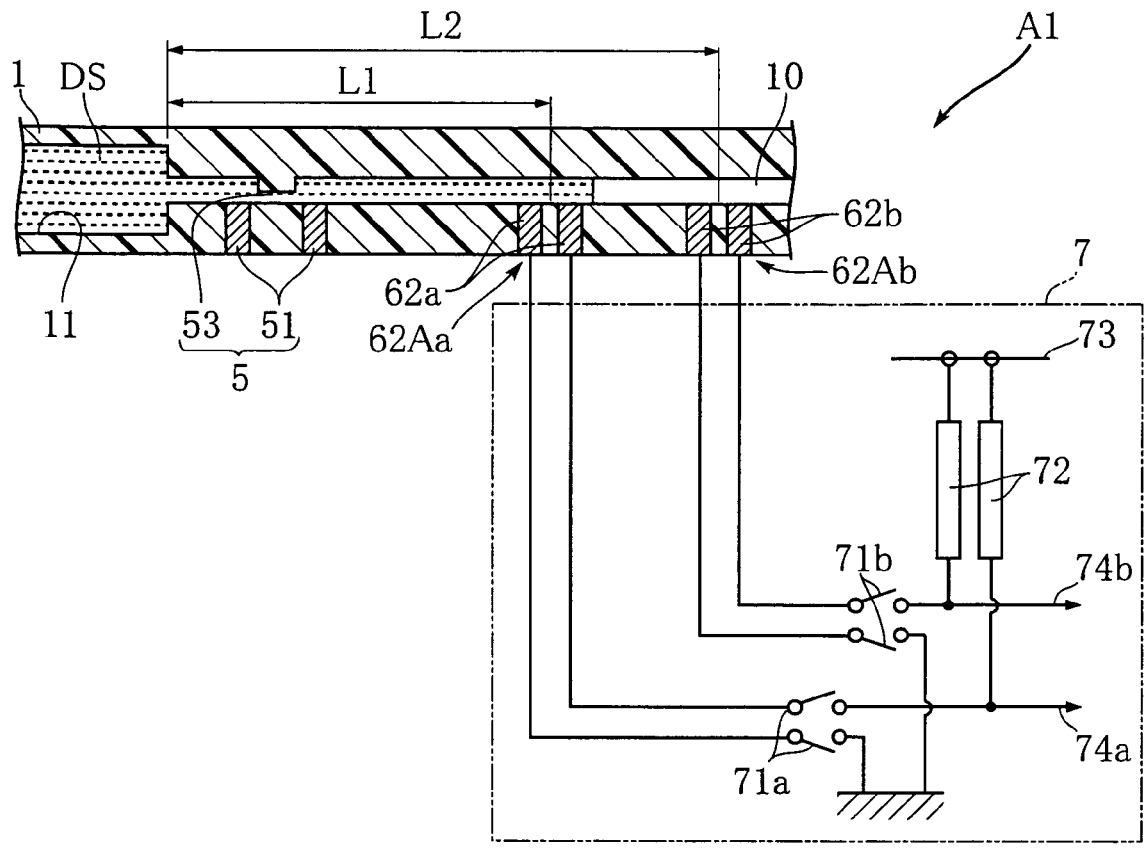
FIG. 1 is a schematic sectional view showing a fine channel flowmeter according to a first embodiment of the present invention.
Figure 2:
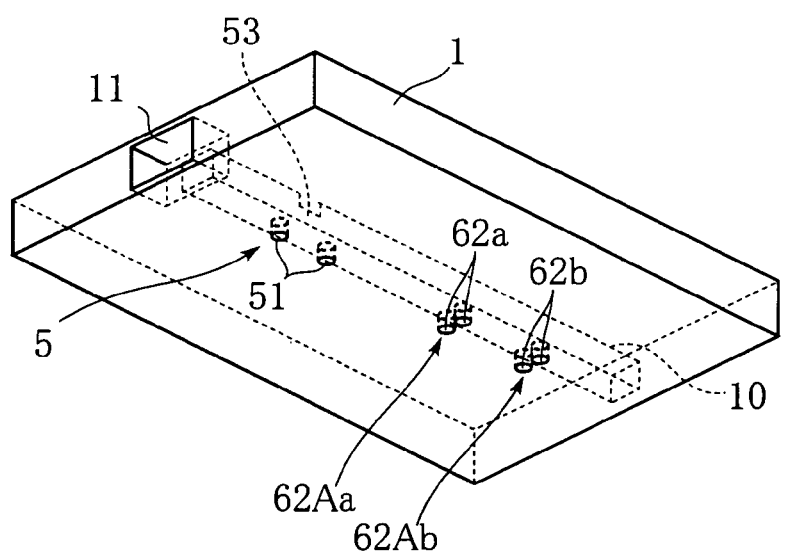
FIG. 2 is an overall perspective view showing the fine channel flowmeter according to the first embodiment of the present invention.

FIGS. 1 and 2 show a fine channel flowmeter according to a first embodiment of the present invention. The flowmeter A1 of this embodiment includes two electrode groups 62Aa, 62Ab and a conduction detector 7. The flowmeter A1 of this embodiment is designed to measure the flow of a blood sample DS. The blood sample DS flows through a channel 10 formed in a main body 1. As shown in FIG. 2, the main body 1 of this embodiment is made of transparent resin such as acrylic resin. The channel 10 penetrates through the main body 1 which is in the form of a flat plate. The channel 10 is provided with a liquid pooling portion 11 and an analysis portion 5 for counting blood cells. The analysis portion 5 includes a pair of electrodes 51 and a hole 53 to perform analysis by electrical resistance measurement. When a blood cell such as a red blood cell or a white blood cell in the blood sample DS a's an insulator passes through the hole 53, the resistance between the paired electrodes 51 increases. By detecting the change in the resistance, the blood cells contained in the blood sample DS passed through the analysis portion 5 is counted.

The two electrode groups 62Aa, 62Ab are arranged downstream from the analysis portion in the flow direction. The two electrode groups 62Aa, 62Ab comprise a pair of electrodes 62a and a pair of electrodes 62b, respectively. At least the upper end of each of the electrodes 62a, 62b is exposed at the channel 10 to come into contact with the blood sample DS. As shown in FIG. 2, the electrodes 62a, 62b extend from the lower surface of the main body 1 to reach the channel 10. The electrodes 62a, 62b of each pair are aligned in a direction perpendicular to the flow direction of the channel 10. In FIG. 1, for easier understanding, the paired electrodes 62a, 62b are schematically illustrated as if arranged in a direction different from that in FIG. 2. The main body 1 and the electrodes 62a, 62b may be formed by insert molding. Specifically, in the molding of the main body 1, the electrodes 62a, 62b are arranged at predetermined positions in a mold. In this state, resin material is loaded into the mold. By solidifying the resin material, the main body 1 provided with the paired electrodes 62a, 62b in a penetrating manner is obtained.

The conduction detector 7 detects that electrical conduction is established between each pair of the electrodes 62a, 62b. The conduction detector 7 includes two pairs of switches 71a, 71b, two resistances 72, a power supply voltage 73, and two signal lines 74a, 74b. One of the paired electrodes 62a of the electrode group 62Aa is connected to ground via the switch 71a. The other electrode 62a of the pair is connected to a signal line 74a via the switch 71a. The power supply voltage 73 is connected to the signal line 74a via the resistance 72. The connection between the electrode group 62b and the switches 71b, the resistance 72, the power supply voltage 73 and the signal line 74b is similar to the above.

The measurement of the flow of the blood sample DS using the flowmeter A1 will be described below.

First, the supply of the blood sample DS from the liquid pooling portion 11 is started. Before the supply of the blood sample DS is started, the analysis portion 5 is made ready for analysis, and the conduction detector 7 is made ready for conduction detection. Specifically, in the conduction detector 7, both of the paired switches 71a and 71b are set closed.

When the front of the blood sample DS passes the analysis portion 5 and reaches the electrode group 62Aa, the counting of blood cells is started. This is because, although the counting of blood cells is possible at the time point when the front of the blood sample DS passes the analysis portion 5, it is necessary to measure the flow of the blood sample DS through the analysis portion 5 in order to count the blood cells per unit volume of the blood sample DS. When the front of the blood sample DS reaches the electrode group 62Aa, the paired electrodes 62a are electrically connected to each other via e.g. the blood plasma of the blood sample DS which is a conductor. By detecting this electrical conduction based on a change in signals of the signal line 74a, the fact that the front of the blood sample DS has reached the electrode group 62Aa is detected.

When the supply of the blood sample DS is continued, the front of the blood sample DS reaches the electrode group 62Ab. This reaching is detected based on a change in signals of the signal line 74b. Thus, the time from when the sample blood DS reached the electrode group 62Aa till when the sample reaches the electrode group 62Ab is measured. This time is represented as T12. The distance between the electrode group 62Aa and the electrode group 62Ab is represented as L2−L1. Then, the average velocity V12 of the flow of the blood sample DS from the electrode group 62Aa to the electrode group 62Ab is obtained by V12=(L2−L1)/T12. When the cross sectional area of the channel 10 is represented as A, the average flow Q12 of the blood sample DS from the electrode group 62Aa to the electrode group 62Ab is obtained by Q12=A×V12. Based on the average flow Q12 and the number of blood cells counted by the analysis portion 5, the number of blood cells per unit volume of the blood sample DS is obtained. When the blood sample DS is diluted blood, the number of blood cells in the blood is obtained based on the dilution ratio.

After the blood sample DS passed the electrode group 62Ab, those of the switches 71a, 71b which are connected to the signal lines 74a, 74b are opened. As a result, the blood sample DS is connected to ground. Alternatively, after the blood sample DS passed the electrode group 62Ab, all the paired switches 71a, 71b may be opened.

The advantages of the flowmeter A1 will be described below.

According to this embodiment, the flow of the blood sample DS through the analysis portion 5 during the analysis by the analysis portion 5 is measured accurately. As compared with an optical part such as a lens, it is easy to make the electrodes 62a, 62b small, which ensures reduction in size of the system including the flowmeter A1. Since both of the paired electrodes 62a and the paired electrodes 62b are aligned in a direction perpendicular to the flow direction of the channel 10 as shown in FIG. 2, deviation does not occur between the timings at which electrical conduction is established between each pair of electrodes 62a, 62b. Further, the channel 10 can be made short by arranging the electrode groups 62Aa and 62Ab close to each other, which is advantageous for reducing the size of the system including the flowmeter A1.

Since the main body 1 is formed integrally, the blood sample DS is prevented from leaking from the channel 10. Thus, the system including the flowmeter A1 is kept hygienic.

Figure 3:
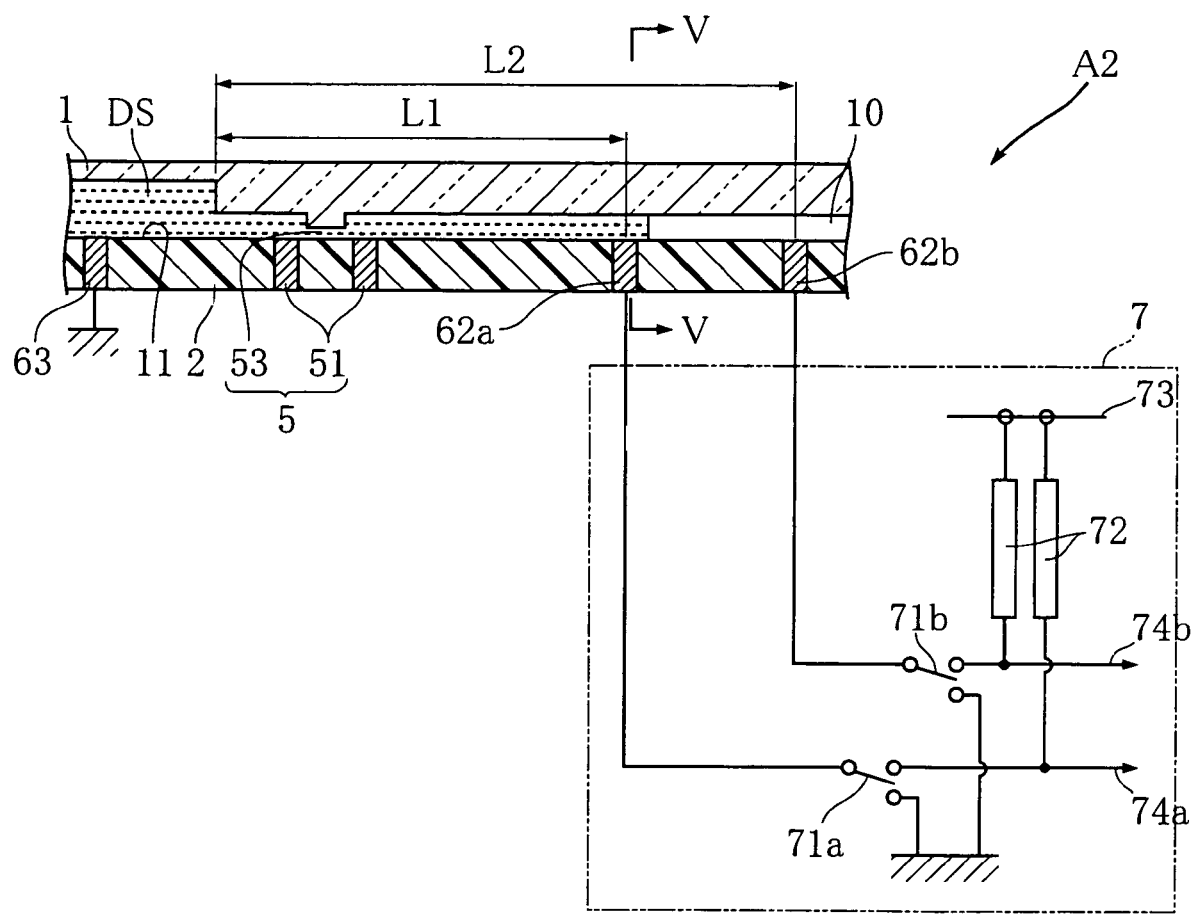
FIG. 3 is a schematic sectional view showing a fine channel flowmeter according to a second embodiment of the present invention.
Figure 4:
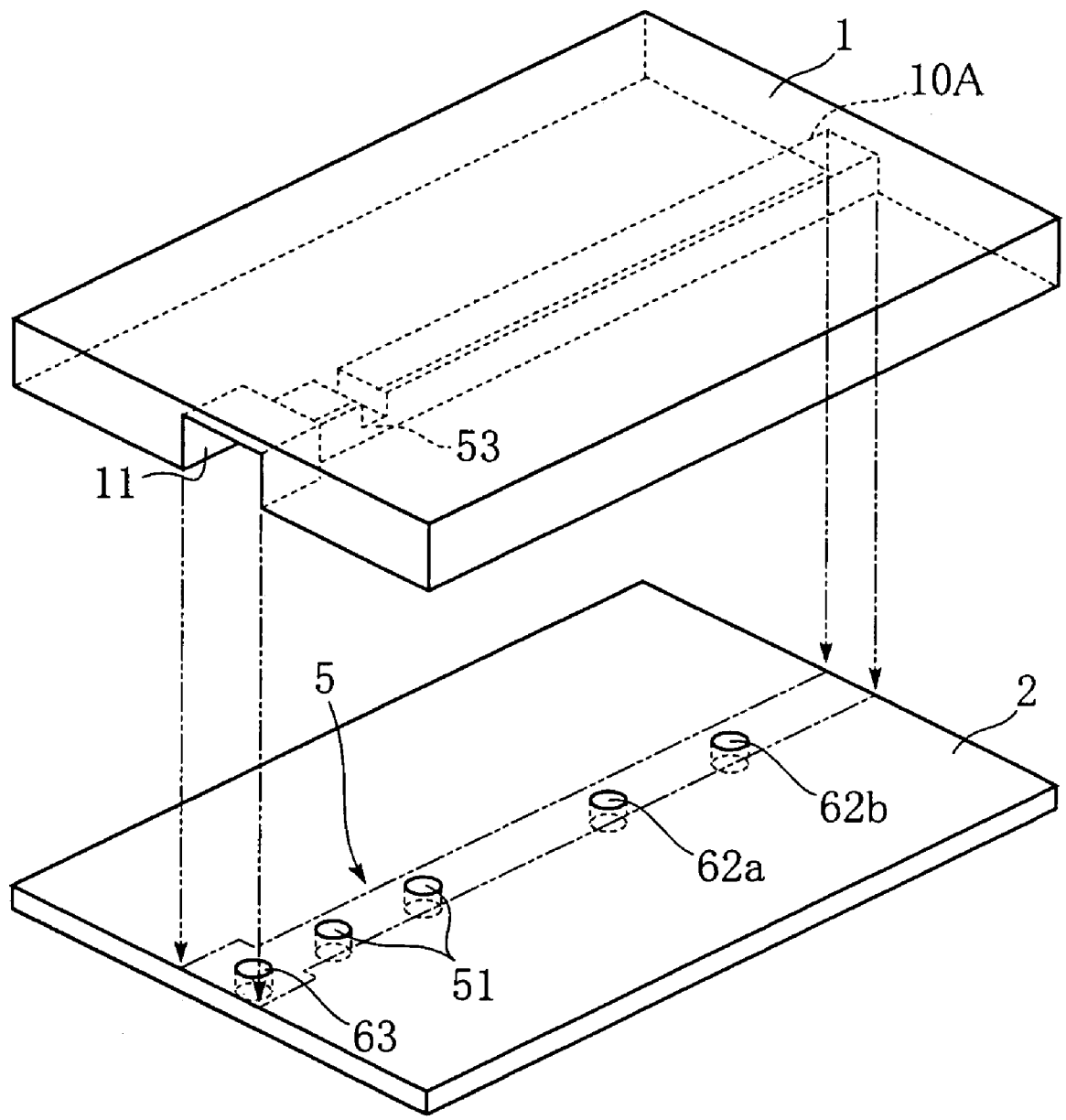
FIG. 4 is an overall perspective view showing the fine channel flowmeter according to the second embodiment of the present invention.

FIGS. 3 and 4 show a fine channel flowmeter according to a second embodiment of the present invention. The flow meter A2 of this embodiment differs from that of the first embodiment in that the flowmeter A2 includes a single electrode 62a, a single electrode 62b and a common electrode 63 and further includes a printed wiring board 2 in addition to the main body 1. In FIG. 3 and the subsequent drawings, the elements which are identical or similar to those of the first embodiment are designated by the same reference signs as those used for the first embodiment.

As shown in FIG. 3, the flowmeter A2 includes the electrode 62a, the electrode 62b and the common electrode 63. The structure of the electrodes 62a, 62b is the same as that described as to the flow meter A1. The electrodes 62a and 62b are connected to signal lines 74a and 74b via switches 71a and 71b, respectively. An end of the common electrode 63 is exposed at the liquid pooling portion 11, whereas the other end of the common electrode is connected to ground. The conduction detector 7 detects the electrical conduction between the common electrode 63 and each of the electrodes 62a, 62b.

Figure 5:
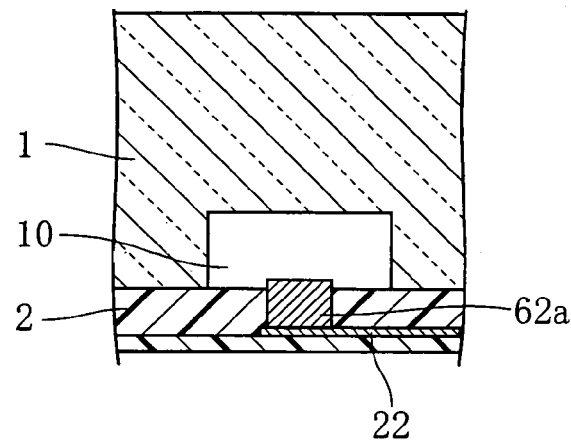
FIG. 5 is a sectional view of a principal portion taken along lines V-V in FIG. 3.

As shown in FIG. 4, the flowmeter A2 of this embodiment is provided in e.g. a cartridge provided by bonding the main body 1 and the printed wiring board 2 together. The main body is formed with a groove 10A to serve as a channel 10. The printed wiring board 2 comprises a plurality of substrates made of e.g. epoxy resin and laminated together. A wiring pattern made of e.g. a copper foil is formed between the substrates. The electrodes 62a, 62b and the common electrode 63 are provided in the printed wiring board 2 at portions to face the groove 10A. The cartridge is obtained by liquid-tightly bonding the main body 1 and the printed wiring board 2 together using e.g. an adhesive. The electrodes 62a, 62b and the common electrode 63 are formed as a so-called through-hole electrode. For instance, as shown in FIG. 5, the electrode 62a penetrates the printed wiring board 2 in the thickness direction, and the lower end of the electrode is connected to a wiring pattern 22. To prevent undesirable electrical conduction of the wiring pattern 22, a protective sheet is bonded to the lower surface of the printed wiring board 22.

First, to measure the flow of the blood sample DS using the flowmeter A2, the switches 71a, 71b are closed to the signal lines 74a, 74b side. When the supply of the blood sample DS is started, the front of the blood sample DS reaches the electrode 62a and then the electrode 62b. The fact that the front of the blood sample DS has reached the electrodes 62a and 62b is detected based on a change in signals of the signal lines 74a and 74b, respectively. By subsequently performing the same process steps as those for the flowmeter A1, the average flow Q12 of the blood sample DS is measured.

In this embodiment again, the flow of the blood sample DS through the analysis portion 5 during the analysis by the analysis portion 5 is measured accurately. The structure is also suitable for the size reduction of the system including the flowmeter A2. Particularly, the structure of this embodiment includes the single electrode 62a and the single electrode 62b, i.e., the number of electrodes to be formed is small. This is advantageous for reducing the size of the system including the flowmeter A2 and simplifying the process for manufacturing the system. Even with the structure including the single electrode 62a and the single electrode 62b, the fact that the blood sample DS has reached the electrode 62a, 62b is properly detected by detecting the electrical conduction between the common electrode 63 and each of the electrodes 62a and 62b.

The position of the electrodes 62a, 62b as through-hole electrodes in the printed wiring board 2 can be set relatively accurately. Even when the channel 10 is made narrower, the electrodes 62a, 62b can be arranged at proper positions in the channel 10. Thus, the structure is suitable for reducing the size of the system including the flowmeter A2.

Figure 6:
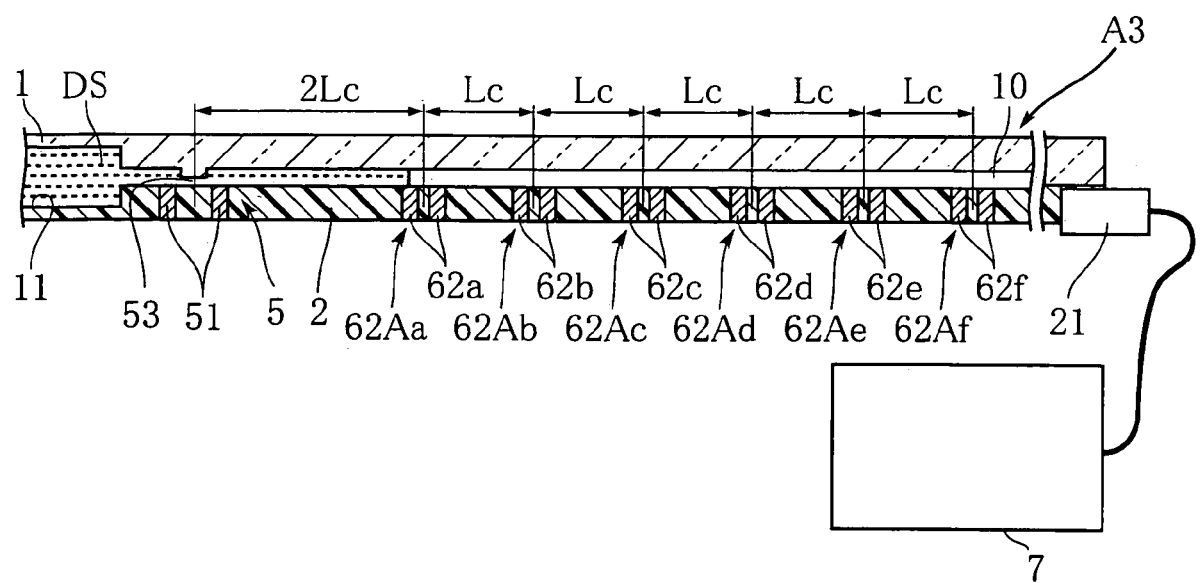
FIG. 6 is a schematic sectional view showing a fine channel flowmeter according to a third embodiment of the present invention.

FIG. 6 shows a fine channel flowmeter according to a third embodiment of the present invention. The flowmeter A3 of this embodiment differs from any of the above described embodiments in that the flowmeter A3 includes a plurality of electrode groups 62Aa-62Af.

The electrode groups 62Aa-62Af are spaced from each other along the flow direction of the channel 10 by a predetermined distance Lc. A pair of electrodes 51 is provided to be spaced from the electrode group 62Aa by a distance 2Lc. Each of the electrode groups 62Aa-62Af comprises a pair of electrodes 62a-62f. The paired electrodes 62a-62f are spaced from each other in a direction perpendicular to the flow direction of the channel 10. For easier understanding, both of the paired electrodes 62a-62f are schematically illustrated to appear in FIG. 6.

A connector 21 is provided at an end of the printed wiring board 2. The electrode groups 62Aa-62Af and the connector 21 are connected to each other via a wiring pattern (not shown) formed on the lower surface of the printed wiring board 2. The connector 21 is connected to the conduction detector 7 via a cable. The conduction detector 7 has the same structure as that described with reference to FIGS. 1-3 and detects electrical conduction in each of the electrode groups 62Aa-62Af.

Adjacent ones of the electrode groups 62Aa-62Af are spaced from each other by the distance Lc. Thus, the flow of the blood sample from when the front of the blood sample DS moves from one of the electrode groups to the adjacent electrode group on the downstream side is equal between any adjacent electrode groups 62Aa-62Af. That is, each time the front of the blood sample reaches one of the electrode groups 62Aa-62Af, it is determined that a predetermined amount of blood sample DS has flowed. By repeating the detection of the flow of the predetermined amount of blood sample DS and the counting of the blood cells by the analysis portion 5, the counting of blood cells per unit volume of the blood sample DS is performed a plurality of times.

With this structure, the flow measurement can be successively performed a plurality of times while counting the blood cells by the analysis portion 5. Thus, the accuracy of measurement of the blood cells per unit volume of the blood sample DS is enhanced. Further, even when the amount of the blood sample DS is relatively small and the blood sample DS does not reach the electrode group 92Af, the blood cells is properly counted when the blood sample DS reaches at least the electrode group 62Ab. Thus, the range of the amount of the blood sample DS to which the system including the flowmeter A3 is applicable is widened.

Figure 7:
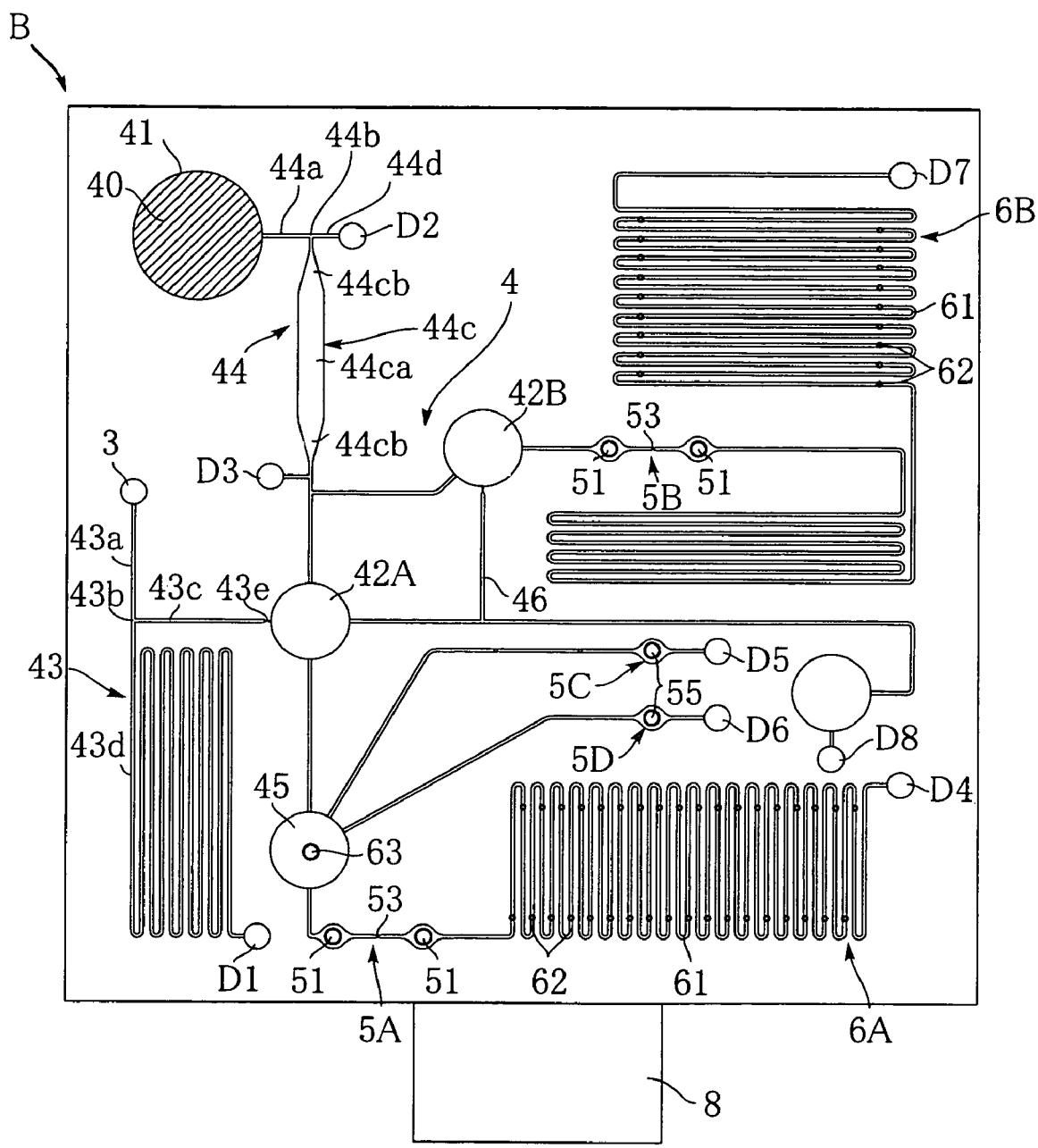
FIG. 7 is an overall plan view showing an example of analyzer cartridge according to the present invention.
Figure 8:
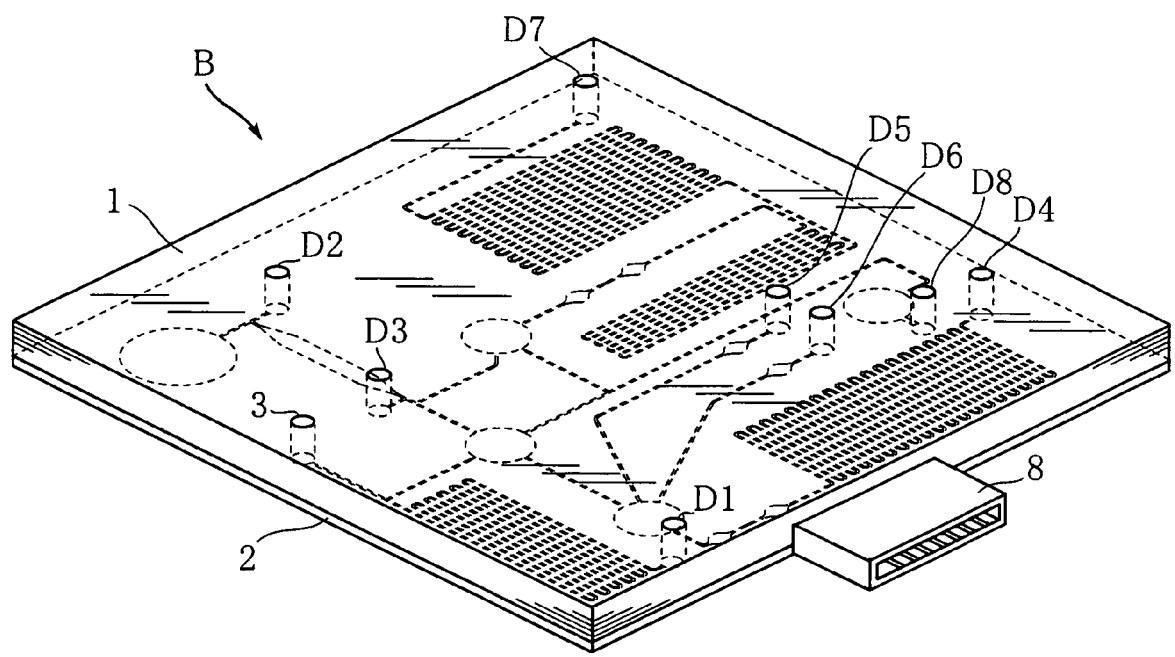
FIG. 8 is an overall perspective view showing an example of analyzer cartridge according to the present invention.
Figure 9:
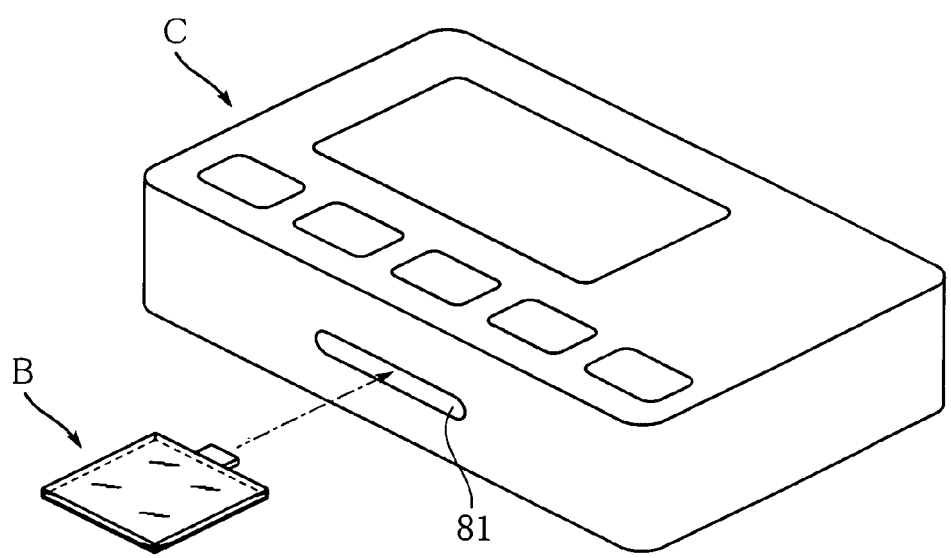
FIG. 9 is an overall perspective view showing an example of analyzer according to the present invention.

FIGS. 7 and 8 show an example of analyzer cartridge according to the present invention. The cartridge B shown in the figures is provided by bonding a main body 1 and a printed wiring board 2 together. The cartridge includes a liquid introduction port 3, a dilution means 4, a plurality of analysis portions 5A, 5B, 5C, 5D and two flow measuring units 6A and 6B. The two flow measuring units 6A and 6B constitute the fine channel flowmeter according to the present invention. As shown in FIG. 9, the cartridge 9 is loaded into a loading port 81 of an analyzer C. The analyzer C is provided with a conduction detector which is similar to the conduction detector 7 shown in FIGS. 1 and 3.

The main body 1 has a flat rectangular configuration and is made of a transparent resin such as acrylic resin. The lower surface of the main body 1 in FIG. 8 is formed with a plurality of recesses or grooves for forming channels or tanks, which will be described later. In this embodiment, the main body 1 has a size of about 70 mm square and a thickness of about 3 mm. The printed wiring board 2 is formed with a plurality of electrodes 51, 62. The printed wiring board 2 has an extension provided with a connector 8. The connector 8 is utilized for connecting the cartridge B to the analyzer C.

The liquid introduction port 3 is provided for introducing the blood to be analyzed into the cartridge B. The liquid introduction port 3 comprises a through-hole formed in the main body 1 and has a diameter of about 3 mm.

The dilution means 4 is provided for diluting the blood introduced from the liquid introduction port 3 to a concentration suitable for various kinds of analysis. The dilution means includes a diluent tank 41, a first and a second dilution tanks 42A, 42B, a-blood measurer 43 and a diluent measurer 44.

The dilution means 4 of this embodiment is designed to perform two-stage dilution using the first and the second dilution tanks 42A and 42B, which will be described later.

The diluent tank 41 is provided for storing diluent 40 for diluting the blood in the cartridge B. The diluent tank 41 has a diameter of about 12 mm and a depth of about 2 mm and is capable of storing about 200 μL of diluent 40.

The blood measurer 43 is arranged between the liquid introduction port 3 and the first dilution tank 42A and includes an introduction channel 43a, a measurement channel 43c, and an overflow channel 43d. The introduction channel 43a is used for introducing blood from the liquid introduction port 3. The introduction channel 43a has a width of about 250 μm and a depth of about 250 μm, so that the width/depth is one. Unless otherwise described, each of the channels described below has the same width and depth as those of the introduction channel 43a. The measurement channel 43c and the overflow channel 43d extend from the introduction channel 43a via a branch portion 43b. The measurement channel 43c is used for temporarily retaining blood by the amount suitable for the analysis. The measurement channel 43c has a length of about 8 mm and a volume of about 0.5 μL. An orifice 43e is provided between the measurement channel 43c and the first dilution tank 42A. The orifice 43e serves to increase the pressure drop resistance from the measurement channel 43c to the first dilution tank 42A. The overflow channel 43d is a meandering path and connected to a drain D1.

The diluent measurer 44 is arranged downstream from the diluent tank 41 and connected to the first and the second dilution tanks 42A and 42B. The diluent measurer 44 includes an introduction channel 44a, a measurement channel 44c, and an overflow channel 44d. The introduction channel 44a is utilized for introducing the diluent 40 from the diluent tank 41. The measurement channel 44c and the overflow channel 44d extend from the introduction channel 44a via a branch portion 44b. The measurement channel 44c is used for temporarily retaining the diluent 40 by a precise amount suitable for diluting the blood to a predetermined concentration. The measurement channel 44c includes a large cross-sectional portion 44ca and two tapered portions 44cb. The large cross-sectional portion 44ca has a width of about 2 mm and a depth of about 2 mm, and the volume is about 50 μL. The two tapered portions 44cb are connected respectively to the front end and the rear end of the large cross-sectional portion 44ca and prevent the flow of the diluent 40 into and out of the large cross-sectional portion 44ca from being disturbed. The overflow channel 44d is connected to a drain D2.

Both of the first and the second dilution tanks 42A and 42B are used for diluting blood and have a diameter of about 6 mm, a depth of about 2 mm and a volume of not less than 50 μL. The first dilution tank 42A is connected to the blood measurer 43 and the diluent measurer 44. The blood measured by the blood measurer 43 is diluted in the first dilution tank 42A with the diluent 40 measured by the diluent measurer 44. The second dilution tank 42B is connected to the first dilution tank 42A and the diluent measurer 44. The blood sample diluted in the first dilution tank 42A is diluted in the second dilution tank 42B with the diluent 40 measured by the diluent measurer 44. A measurement channel 46 is provided between the first dilution tank 42A and the second dilution tank 42B.

The analysis portions 5A, 5B, 5C, 5D are portions to perform the analysis of a particular component in the blood. The first and the second analysis portions 5A and 5B are designed to perform the analysis by electrical resistance measurement. The first analysis portion 5A is for white blood cells, whereas the second analysis portion 5B is for red blood cells. The third and the fourth analysis portions 5C and 5D are designed to perform analysis by an optical method. The third analysis portion 5C is for Hb, whereas the fourth analysis portion is for CRP.

The first analysis portion 5A is connected to the first dilution tank 42A via a buffer tank 45. The white blood cells are counted in the first analysis portion 5A by using the blood sample diluted in the first dilution tank 42A. The first analysis portion 5A includes a hole 53 and a pair of electrodes 51 arranged on the opposite sides of the hole 53 to perform the counting by electrical resistance measurement. While the width of the channel on the opposite sides of the hole 53 is about 250 μm, the hole 53 has a relatively small width of about 50 μm. The channel includes portions enlarged into a generally circular shape on the opposite sides of the hole 53, at which the paired electrodes 51 are provided. The second analysis portion 5B is connected to the second dilution tank 42B. The red blood cells are counted in the second analysis portion 5B by using the blood sample after the second dilution in the second dilution tank 42B. The structure of the second analysis portion 5B is substantially the same as that of the first analysis portion 5A. The buffer tank 45 is provided with a common electrode 63.

Each of the third and the fourth analysis portions 5C and 5D is independently connected to the buffer tank 45. Each of the third and the fourth analysis portions 5C and 5D includes a reflection film 55 provided at a portion of the channel enlarged into a generally circular shape. The third and the fourth analysis portions are designed to measure Hb and CRP, respectively, by an optical method. In this embodiment, light impinges on the third and the fourth analysis portions 5C and 5D through the main body 1, which is transparent. By detecting the reflected light, Hb and CRP are measured.

The flow measuring units 6A and 6B are connected to the first and the second analysis portions 5A and 5B, respectively. The flow measuring units 6A and 6B measure the flow of the blood sample through the first and the second analysis portions 5A and 5B, respectively. Each of the flow measuring units includes a meandering channel 61 and a plurality of electrodes 62. The meandering channel 61 is provided to increase the length in the flow direction and has a sufficient volume. In this embodiment, the meandering channel 61 serves as a storage means capable of storing at least 50 μL of blood sample after the analysis at the first or the second analysis portion 5A or 5B. The plurality of electrodes 62 are arranged at a predetermined pitch in the flow direction of the meandering channel 61. The electrodes 62 are connected to the conduction detector (not shown) described in the first through the third embodiments.

The blood analysis using the cartridge B will be described below.

First, referring to FIG. 7, blood as the sample liquid is introduced into the cartridge from the liquid introduction port 3 by using e.g. a dropper. Then, as shown in FIG. 9, the cartridge B, into which blood is introduced, is mounted to an analyzer C. In the mounting process, the connector 8 is connected to a connector (now shown) of the analyzer C.

Then, the blood is measured by the blood measurer 43. By this measurement, a predetermined amount, i.e., about 0.5 μL of blood is retained in the first dilution tank 42A. The diluent 40 is measured by the diluent measurer 44. By this measurement, a predetermined amount, i.e., about 50 μL of diluent 40a is retained in the first dilution tank 42A. Then, about 0.5 μL of blood and about 50 μL of diluent 40a are mixed within the first dilution tank 42A to provide blood sample as a 1:100 diluted sample liquid. The mixing may be performed by rotating a stirrer (not shown) incorporated in the first dilution tank 42A within the first dilution tank 42A by utilizing magnetic force. The above-described dilution is hereinafter referred to as the first dilution.

After the first dilution in the first dilution tank 42A is completed, the white blood cells are counted in the first analysis portion 5A, and Hb and CRP are measured in the third and the fourth analysis portions 5C and 5D. As shown in FIG. 7, the buffer tank 45 is connected to the first dilution tank 42A. The above-described 1:100 diluted blood sample is supplied to the buffer tank 45.

Figure 10:
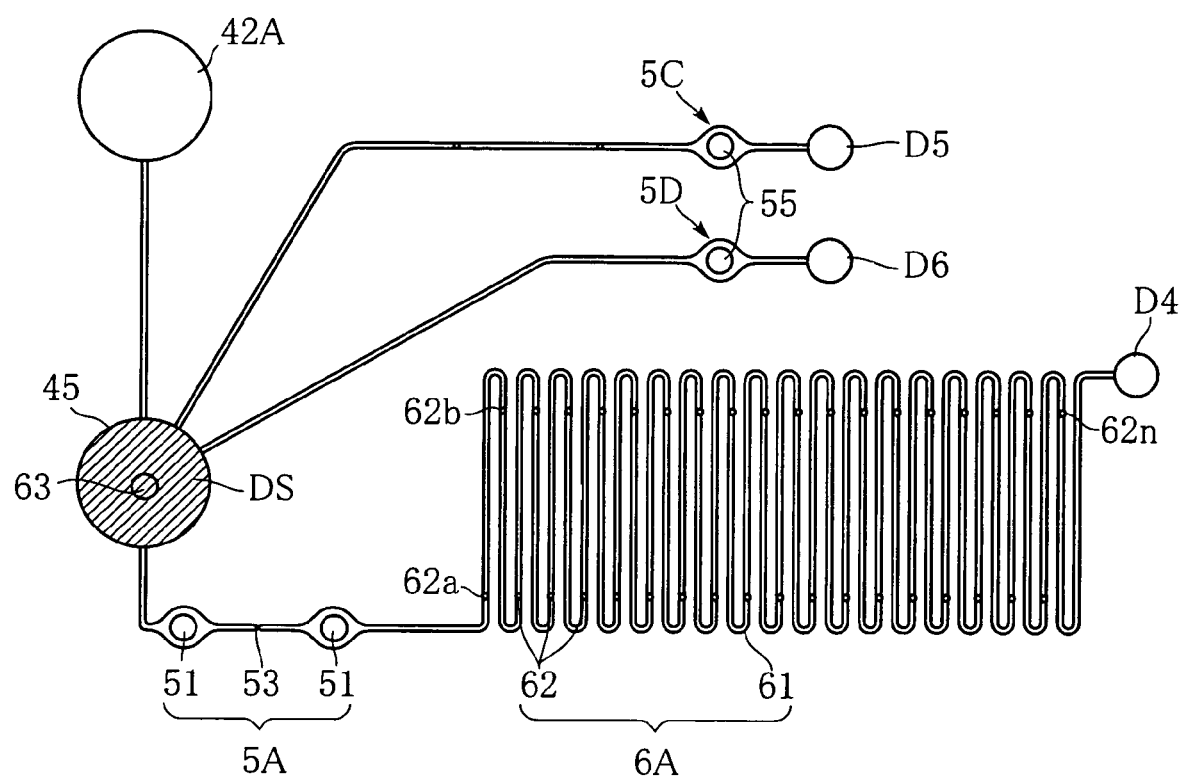
FIG. 10 is a plan view showing the initial state in the blood cell counting process using an example of analyzer cartridge according to the present invention.
Figure 11:
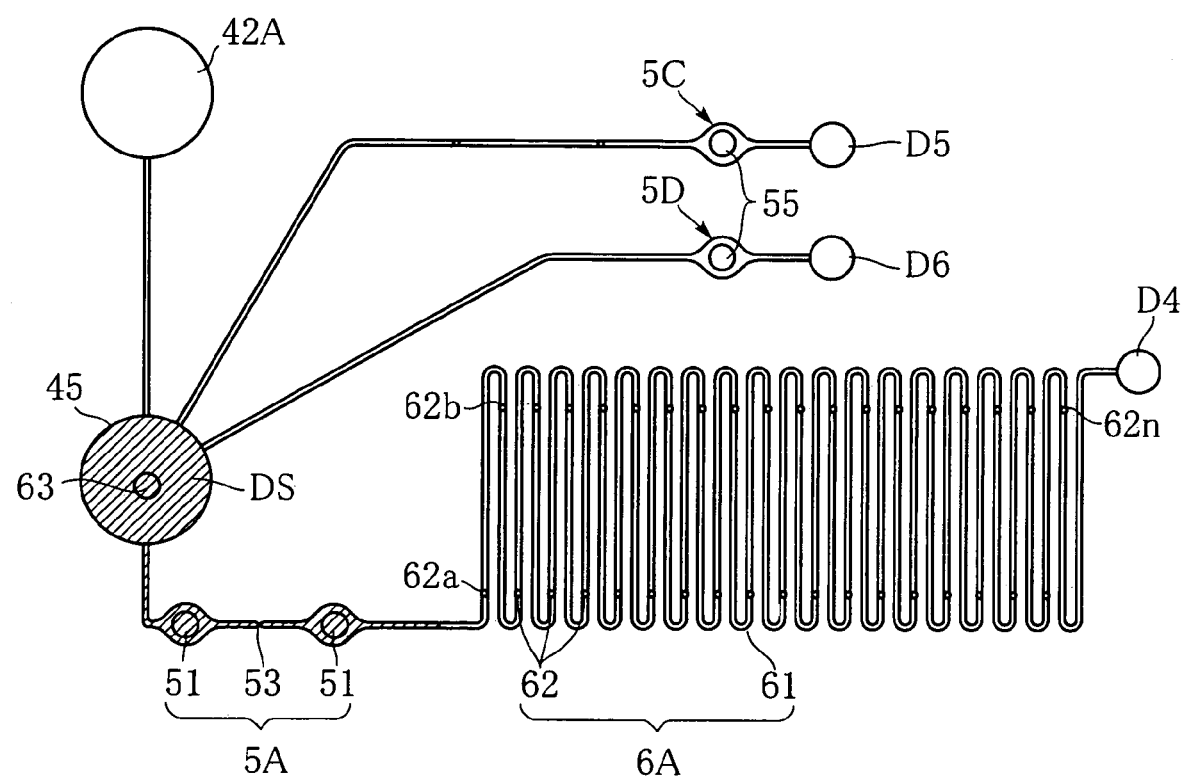
FIG. 11 is a plan view showing the state in which the blood sample has reached the first analysis portion in the blood cell counting process using an example of analyzer cartridge according to the present invention.

The process for counting the white blood cells in the first analysis portion 5A using part of the blood sample stored in the buffer tank 45 will be described below with reference to FIGS. 10-14. This counting is performed using the first analysis portion 5A and the first flow measuring unit 6A arranged on the downstream side of the first analysis portion. FIG. 10 shows the state to start the counting of the white blood cells. In this state, the blood sample DS as the 1:100 diluted sample liquid is retained in the buffer tank 45. In this state, suction of air from e.g. the drain D4 is started. As a result, as shown in FIG. 11, the blood sample DS flows out of the buffer tank 45 to flow through the first analysis portion 5A.

Figure 12:
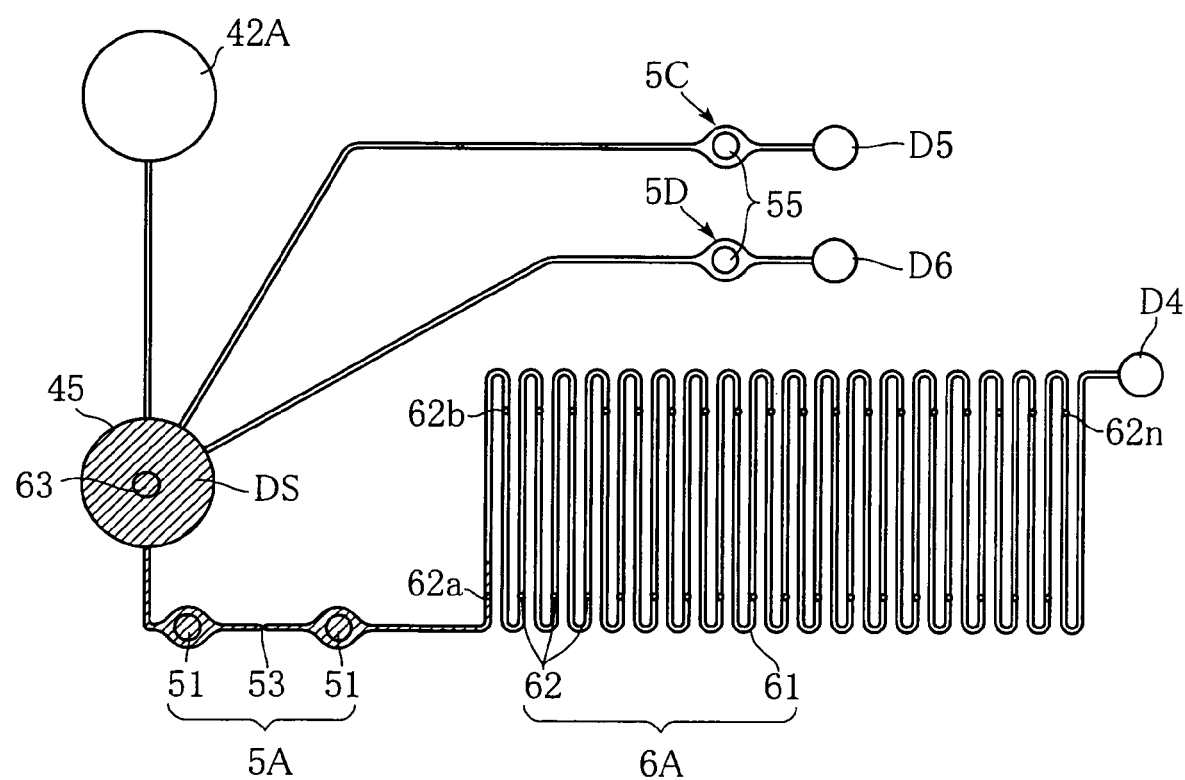
FIG. 12 is a plan view showing the start state in the blood cell counting process using an example of analyzer cartridge according to the present invention.

When the suction from the drain D4 is further continued, the front of the blood sample DS reaches the electrode 62a which is positioned on the most upstream side among the plurality of electrodes 62, as shown in FIG. 12. The fact that the front of the blood sample DS has reached the electrode 62a is detected by monitoring the electrical conduction between the common electrode 63 and the electrode 62a. Based on the detection, the counting of the white blood cells by the first analysis portion 5A is started.

Figure 13:
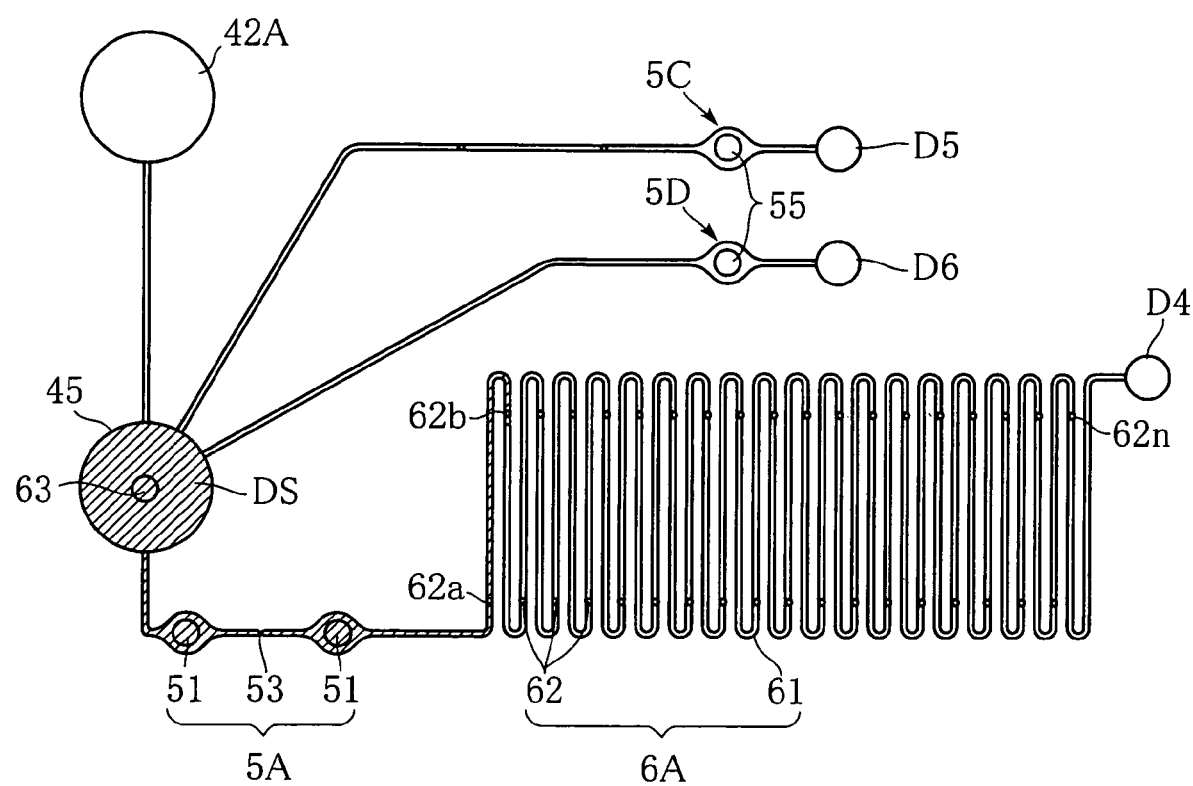
FIG. 13 is a plan view showing the state in which the front of the blood sample has reached the second electrode from the upstream side in the blood cell counting process using an example of analyzer cartridge according to the present invention.

When the suction is continued, the front of the blood sample DS reaches the electrode 62b which is the second among the plurality of electrodes 62 from the upstream side, as shown in FIG. 13. The reaching is detected by monitoring the electrical conduction between the common electrode 63 and the electrode 62b, for example. The flow of the blood sample DS through the first analysis portion 5A during the period from when the front of the blood sample DS reaches the electrode 62a until the front reaches the electrode 62b is equal to the amount of the blood sample DS which can be retained between the electrodes 62a and 62b. Since the distance between the electrodes 62a and 62b along the flow direction is known, the flow of the blood sample DS which has passed through the first analysis portion 5A is determined. Based on this flow and the integrated number of white blood cells, the number of white blood cells per unit volume of the blood sample DS is determined. Based on this, the number of white blood cells per unit volume of the blood is determined.

Figure 14:
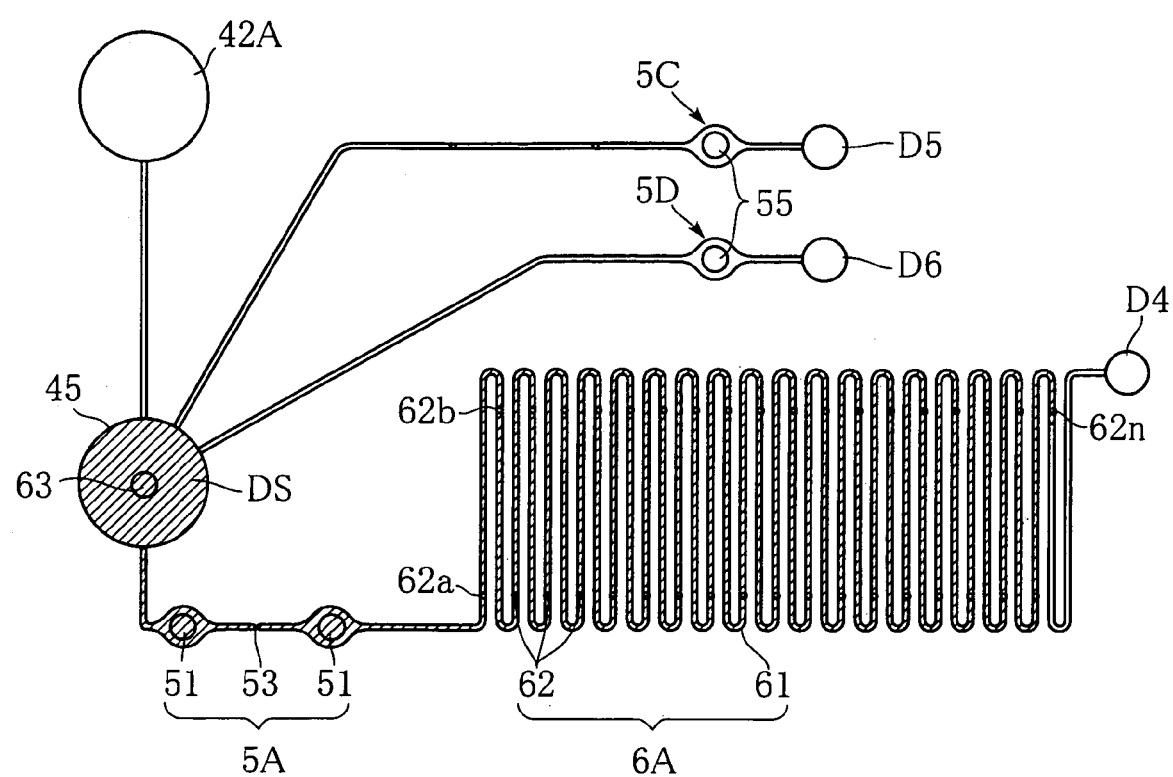
FIG. 14 is a plan view showing the state in which the front of the blood sample has reached the most downstream electrode in the blood cell counting process using an example of analyzer cartridge according to the present invention.
Figure 15:
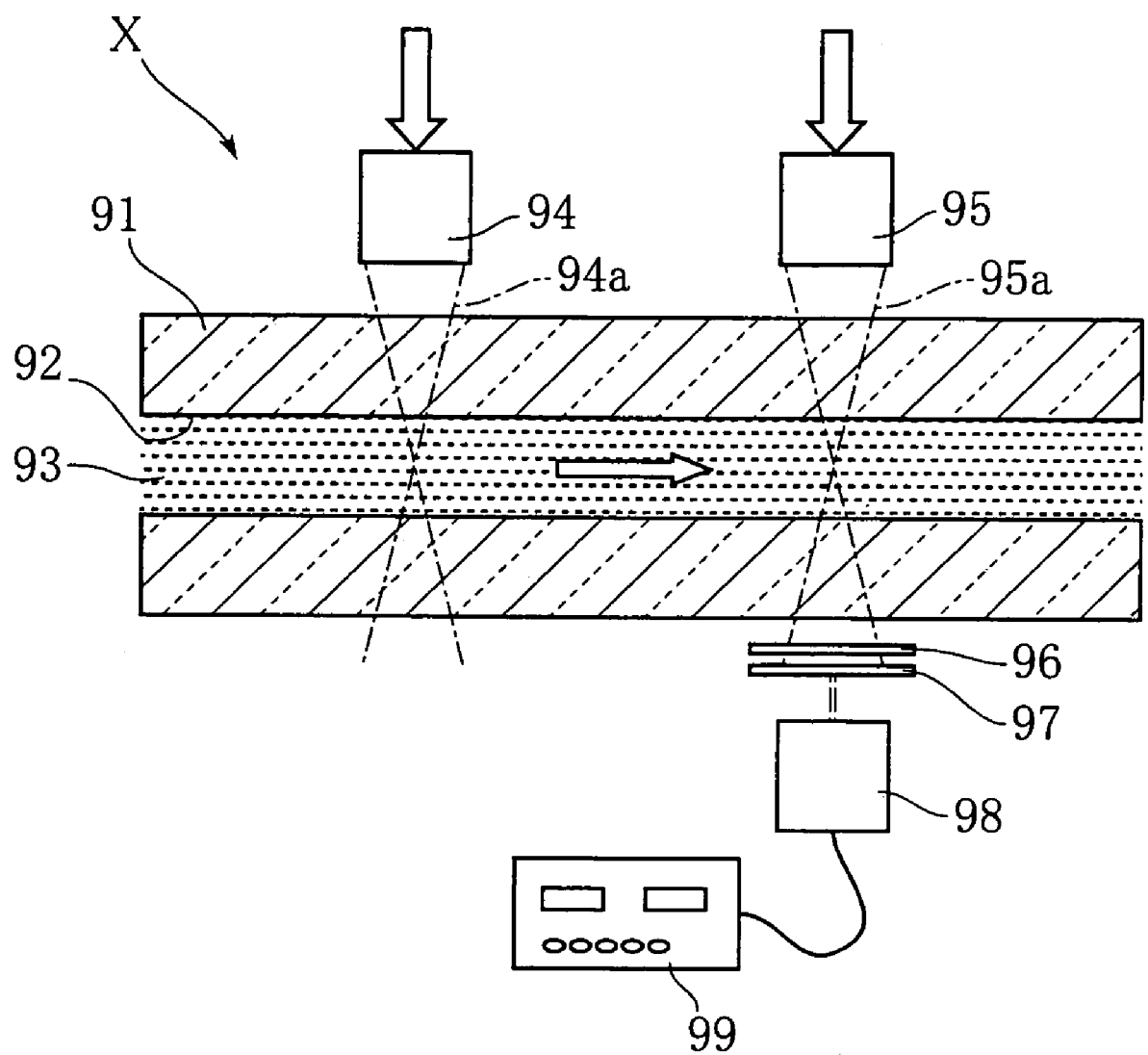
FIG. 15 is a schematic sectional view showing an example of conventional fine channel flowmeter.

After the above-described process, the counting may be repeated while continuing the suction to increase the accuracy of the counting. In this embodiment, the first flow measuring unit 6A is provided with a plurality of electrodes 62. Therefore, the counting can be performed a plurality of times by storing the number of white blood cells every time the front of the blood sample DS reaches each of the electrodes 62 on the downstream side of the electrodes 62a, 62b. This is equivalent to the counting of the white blood cells using a larger amount of blood sample DS, so that the accuracy of counting is enhanced. The counting by the first analysis portion 5A may be stopped when it is detected that the front of the blood sample DS has reached the electrode 62n located on the most downstream side among the electrodes 62, as shown in FIG. 14. As will be understood from the figure, when the counting by the first analysis portion 5A is finished, the blood sample DS after the analysis remains within the meandering channel 61.

The analysis by the third and the fourth analysis portions 5C and 5D may be performed by performing suction from the drains D5 and D6 to cause the blood sample DS to reach the respective reflection films 55 of the third and the fourth analysis portions 5C and 5D after the counting by the first analysis portion 5A is finished.

The process for counting the red blood cells by the second analysis portion 5B will be described below. Before the counting process, the second dilution is performed by the dilution means 4 shown in FIG. 7. In the first dilution, the blood is diluted about 1:100 with the diluent 40. In the second dilution, on the other hand, the 1:100 diluted blood sample DS obtained by the first dilution is further diluted about 1:100 with the diluent 40. Thus, in the second dilution tank 42B, substantially 1:10000 dilution is performed using 5 μL of blood sample DS and about 50 μL of diluent 40.

The red blood cells are counted by the second analysis portion 5B using the 1:10000 diluted blood sample obtained by the above-described process. The counting is performed in a substantially same manner as the counting performed by the first analysis portion 5A. The measurement of the flow utilizing the second flow measuring unit 6B is performed similarly to that utilizing the first flow measuring unit 6A.

The advantages of the cartridge B and the analyzer C will be described below.

Similarly to the flow measurement using the flowmeter according to the first through the third embodiments, the flow measurement using the first and the second flow measuring units 6A and 6B is very easy and accurate. Thus, the counting of red blood cells and white blood cells is performed accurately. Further, the flow of e.g. the blood sample DS is measured accurately even when the flow of the blood sample DS varies with time. Thus, it is unnecessary to provide a mechanism for keeping constant flow in the analyzer C, which is advantageous for simplifying the analyzer C. Particularly, the holes 53 of the analysis portions 5A, 5B cause large pressure drop. It is difficult to cause fluid to flow at a constant flow rate through the channel including the portion with a large pressure drop. According to this embodiment, however, it is unnecessary to achieve a constant flow rate, which is suitable for performing the analysis using the analysis portions 5A, 5B including the holes 53.

The cartridge B does not include a part for flow measurement such as an optical part which cannot be easily reduced in size. The use of a flowmeter utilizing an electrode is advantageous for the size reduction of the cartridge B. Thus, the cartridge B can be suitably designed as a disposable cartridge.

The fine channel flowmeter, the analyzer using the flowmeter and the analyzer cartridge according to the present invention are not limited to the foregoing embodiments. The specific structure of each part of the fine channel flowmeter, the analyzer using the flowmeter and the analyzer cartridge according to the present invention may be varied in design in many ways.

In the fine channel flowmeter according to the present invention, the number of electrode groups or electrodes is not limited to the above-described embodiments and may be determined depending on e.g. the kind of the fluid as the target of the flow measurement or the structure of the channel.

The material of the main body is not limited to a transparent one but may be partially opaque. In this case, at least the portion corresponding to the optical analysis portion is made transparent. Although the use of a printed wiring board is preferable for thickness reduction, a rigid substrate may be used.

The analyzer and the analyzer cartridge according to the present invention are not limited to those having a function to count blood cells and may be designed to analyze various kinds of sample liquid.

The invention claimed is:

1. A fine channel flowmeter for measuring an amount of fluid through a fine channel, the flowmeter comprising:
    at least two electrode groups each including a pair of electrodes; and
    a conduction detector for detecting electrical conduction between the paired electrodes included in each of the electrode groups;
    wherein each of the electrodes is exposed at least partially in the fine channel; and
    wherein the electrode groups are spaced from each other in a flow direction of the fine channel; and
    wherein the flowmeter further comprises a main body in the form of a flat plate formed with the fine channel.

2. The fine channel flowmeter according to claim 1, wherein the paired electrodes are spaced from each other in a width direction of the fine channel.

3. A fine channel flowmeter for measuring an amount of fluid through a fine channel, the flowmeter comprising:
    at least two electrodes; and
    a conduction detector for detecting electrical conduction between said at least two electrodes;
    wherein said at least two electrodes are exposed at least partially in the fine channel and spaced from each other in a flow direction of the fine channel; and
    wherein the flowmeter further comprises a main body in the form of a flat plate formed with the fine channel.

4. The fine channel flowmeter according to claim 3, further comprising a common electrode arranged upstream from said at least two electrodes in the flow direction of the fine channel and coming into contact with the fluid at least partially,
    wherein the conduction detector further detects electrical conduction between the common electrode and each of the electrodes.

5. An analyzer cartridge to be mounted to an analyzer for analyzing a particular component contained in a sample liquid, the cartridge comprising:
    an analysis portion for analyzing the particular component;
    a fine channel connected to the analysis portion; and
    a fine channel flowmeter for measuring an amount of the sample liquid through the fine channel;
    wherein the flowmeter comprises at least two electrode groups each including a pair of electrodes, and a conduction detector for detecting electrical conduction between the paired electrodes included in each of the electrode groups;
    wherein each of the electrodes is exposed at least partially in the fine channel;
    wherein the electrode groups are spaced from each other in a flow direction of the fine channel;
    wherein the cartridge includes a main body in the form of a flat plate in which the fine channel is formed to penetrate; and
    wherein the electrode penetrates from a surface of the main body to the fine channel.

6. An analyzer cartridge to be mounted to an analyzer for analyzing a particular component contained in a sample liquid, the cartridge comprising:
    an analysis portion for analyzing the particular component;
    a fine channel connected to the analysis portion; and
    a fine channel flowmeter for measuring an amount of the sample liquid through the fine channel;

wherein the flowmeter comprises at least two electrode groups each including a pair of electrodes, and a conduction detector for detecting electrical conduction between the paired electrodes included in each of the electrode groups;

wherein each of the electrodes is exposed at least partially in the fine channel;

wherein the electrode groups are spaced from each other in a flow direction of the fine channel;

wherein the cartridge includes a main body in the form of a flat plate formed with a groove for defining the fine channel, and a printed wiring board bonded to a surface of the main body on a side formed with the groove; and wherein the electrode comprises a through-hole electrode formed in the printed wiring board.

7. An analyzer cartridge to be mounted to an analyzer for analyzing a particular component contained in a sample liquid, the cartridge comprising:

an analysis portion for analyzing the particular component;
a fine channel connected to the analysis portion; and
a fine channel flowmeter for measuring an amount of the sample liquid through the fine channel;

wherein the flowmeter comprises at least two electrodes, and a conduction detector for detecting electrical conduction between said at least two electrodes;

wherein said at least two electrodes are exposed at least partially in the fine channel and spaced from each other in a flow direction of the fine channel;

wherein the cartridge includes a main body in the form of a flat plate in which the fine channel is formed to penetrate; and wherein the electrode penetrates from a surface of the main body to the fine channel.

8. An analyzer cartridge to be mounted to an analyzer for analyzing a particular component contained in a sample liquid, the cartridge comprising:

an analysis portion for analyzing the particular component;
a fine channel connected to the analysis portion; and
a fine channel flowmeter for measuring an amount of the sample liquid through the fine channel;

wherein the flowmeter comprises at least two electrodes, and a conduction detector for detecting electrical conduction between said at least two electrodes;

wherein said at least two electrodes are exposed at least partially in the fine channel and spaced from each other in a flow direction of the fine channel;

wherein the cartridge includes a main body in the form of a flat plate formed with a groove for defining the fine channel, and a printed wiring board bonded to a surface of the main body on a side formed with the groove; and wherein the electrode comprises a through-hole electrode formed in the printed wiring board.

9. A fine channel flowmeter for measuring a fluid through a fine channel, the flowmeter comprising:

a first measuring portion for determining an amount of a particular component contained in the fluid, and a second measuring portion for determining a flow rate of the fluid through the fine channel;

wherein the first measuring portion and the second measuring portion are spaced from each other in a flow direction of the fine channel;

wherein the second measuring portion comprises at least two electrodes, and a conduction detector for detecting electrical conduction between said at least electrodes; and wherein said at least two electrodes are exposed at least partially in the fine channel and spaced from each other in a flow direction of the fine channel.

10. The fine channel flowmeter according to claim 9, wherein the first measuring portion comprises a constricted path portion of the fine channel, the first measuring portion further comprising an additional pair of electrodes exposed in the fine channel, one of the additional pair of electrodes exposed in the fine channel, one of the additional pair of electrodes being arranged upstream from the constricted path portion of the fine channel, the other of the additional pair of electrodes being arranged downstream from the constricted path portion of the fine channel.

11. A fine channel flowmeter for measuring a fluid through a fine channel, the flowmeter comprising:

a first measuring portion for determining an amount of a particular component contained in the fluid, and a second measuring portion for determining a flow rate of the fluid through the fine channel;

wherein the first measuring portion and the second measuring portion are spaced from each other in a flow direction of the fine channel;

wherein the second measuring portion comprises at least two electrode groups each including a pair of electrodes, and a conduction detector for detecting electrical conduction between the paired electrodes included in each of the electrode groups;

wherein each of the electrodes is exposed at least partially in the fine channel; and wherein the electrode groups are spaced from each other in the flow direction of the fine channel.

12. The fine channel flowmeter according to claim 11, wherein the first measuring portion comprises a constricted path portion of the fine channel, the first measuring portion further comprising an additional pair of electrodes exposed in the fine channel, one of the additional pair of electrodes being arranged upstream from the constricted path portion of the fine channel, the other of the additional pair of electrodes being arranged downstream from the constricted path portion of the fine channel.

\* \* \* \* \*